US009528086B2

(12) United States Patent
Locht et al.

(10) Patent No.: US 9,528,086 B2
(45) Date of Patent: Dec. 27, 2016

(54) **RECOMBINANT *BORDETELLA* STRAINS**

(71) Applicants: Institut National de la Sante et de la Recherche Medicale (INSERM), Paris (FR); Institut Pasteur de Lille, Lille (FR); Universite Droit et Sante Lille II, Lille (FR)

(72) Inventors: Camille Locht, Brussels (BE); Nathalie Mielcarek, Blandain (BE); Hana Kammoun, La Madeleine (FR)

(73) Assignees: UNIVERSITÉ DROIT ET SANTÉ LILLE II, Lille (FR); INSERM, Paris (FR); INSTITUT PASTEUR DE LILLE, Lille (FR)

( * ) Notice: Subject to any disclaimer, the term of this patent is extended or adjusted under 35 U.S.C. 154(b) by 0 days.

(21) Appl. No.: 14/682,155

(22) Filed: Apr. 9, 2015

(65) Prior Publication Data

US 2015/0210978 A1 Jul. 30, 2015

Related U.S. Application Data

(63) Continuation of application No. PCT/EP2013/071724, filed on Oct. 17, 2013.

(30) Foreign Application Priority Data

Oct. 17, 2012 (EP) .................................... 12306279

(51) Int. Cl.

| | |
|---|---|
| ***C12N 1/36*** | (2006.01) |
| ***A61K 39/02*** | (2006.01) |
| ***C07K 14/235*** | (2006.01) |
| ***A61K 39/09*** | (2006.01) |
| ***A61K 39/12*** | (2006.01) |
| *A61K 39/00* | (2006.01) |

(52) U.S. Cl.

CPC ............... *C12N 1/36* (2013.01); *A61K 39/092* (2013.01); *A61K 39/099* (2013.01); *A61K 39/12* (2013.01); *C07K 14/235* (2013.01); *A61K 2039/522* (2013.01); *A61K 2039/523* (2013.01); *A61K 2039/543* (2013.01); *C12N 2760/16134* (2013.01); *C12N 2760/18534* (2013.01)

(58) Field of Classification Search

None

See application file for complete search history.

(56) References Cited

U.S. PATENT DOCUMENTS

| | | | |
|---|---|---|---|
| 6,713,072 | B1 | 3/2004 | Pizza |
| 6,841,358 | B1 | 1/2005 | Locht |
| 2005/0147607 | A1 | 7/2005 | Reed |
| 2009/0246222 | A1 | 10/2009 | Locht |
| 2010/0111996 | A1 | 5/2010 | Leclerc |
| 2012/0121647 | A1 | 5/2012 | Alonso |
| 2013/0183336 | A1 | 7/2013 | Locht |

FOREIGN PATENT DOCUMENTS

| | | |
|---|---|---|
| EP | 2442826 | 4/2012 |
| FR | 2718750 | 10/1995 |
| WO | 9816553 | 4/1998 |
| WO | 03102170 | 12/2003 |
| WO | 2007104451 | 9/2007 |
| WO | 2008156753 | 12/2008 |
| WO | 2010125014 | 11/2010 |
| WO | 2010146414 | 12/2010 |
| WO | 2013066272 | 5/2013 |
| WO | 2014060514 | 4/2014 |

OTHER PUBLICATIONS

Rui et al Vaccine, 29(33):5502-5511, May 14, 2011.*

Locht, Camille, et al: "Common accessory genes for the Bordetella pertussis filamentous hemagglutinin and fimbriae share sequence similarities with the papC and papD gene families," The EMBO Journal, 1992, vol. 11(9):3175-3183.

Locht, Camille et al: "Bordetalla pertussis, molecular pathogenesis under multiple aspects," Current Opinion in Microbiology, 2001, vol. 4:82-89.

Kashimoto, Takashige, et al: "Identification of functional domains of Bordetella dermonecrotizing toxin," Infect. Immun., 1999, vol. 67(8):3727-3732.

Kavanagh, H. et al: "Attenuated bordetella pertussis vaccine strain BPZE1 modulates allergen-induced immunity and prevents allergic pulmonary pathology in a murine model," Clinical & Experimental Allergy, 2010, vol. 40(933-941.

Ho, Si Ying et al: "Highly attenuated Bordetella pertussis Strain BPZE1 as a potential live vehicle for delivery of heterologous vaccine candidates," Infection and Immunity, 2008, vol. 76:111-119.

Higgins, Sarah C. et al: "Toll-like receptor 4-mediated innate IL-10 activates antigen-specific regulatory T cells and confers resistance to Bordetella pertussis by inhibiting inflammatory pathology," The Journal of Immunology, 2003, vol. 171:3119-3127.

Feunou, Pascal et al: "Genetic stability of the live attenuated Bordetella pertussis vaccine candidate BPZE1," Vaccine, 2008, vol. 28:5722-5727.

Ennis, D.P. et al: "Prior Bordetella pertussis infection modulates allergen priming and the severity of airway pathology in a murine model of allergic asthma," Clin Exp Allergy, 2004, vol. 34:1488-1497.

Ennis, D.P. et al: Whole-cell pertussis vaccine protects against Bordetella pertussis exacerbation of allergic asthma, Immunology Letters 97, 2005, pp. 91-100.

Das, Pam: "Whopping cough makes global comeback," The Lancet Infectious Diseases, 2002, vol. 2:322.

Coppens, Isabelle et al: "Production of Neisseria meningitidis transferrin-binding protein B by recombinant Bordetella pertussis," Infection and Immunity, 2001, pp: 5440-5446.

(Continued)

*Primary Examiner* — Patricia Duffy

(74) *Attorney, Agent, or Firm* — Stanley A. Kim

(57) ABSTRACT

A genetically attenuated *Bordetella pertussis* strain includes a mutated pertussis toxin (ptx) gene, and a heterologous ampG gene, and a hybrid protein including the N-terminal fragment of filamentous haemagglutinin (FHA) and a heterologous epitope or antigenic protein or protein fragment, different from FHA. The strain can be used in an attenuated vaccine for the treatment or prophylaxis of an infectious disease.

13 Claims, 3 Drawing Sheets

(56) References Cited

OTHER PUBLICATIONS

Child Innovac; European Network on Nasal Vaccination against Respiratory Infections in Young Children, 2008, http://www.ist-world.org/ProjectDetails.aspx?; last accessed on Jan. 6, 2015.
Carbonetti, Nicholas H.: "Immunomodulation in the pathogenesis of Bordetella pertussis infection and disease," Current Opinion in Pharmacology, 2007, vol. 7:272-278.
Antoine, R. and C. Locht: "Roles of the disulfide bond and the carboxy-terminal region of the S1 subunit in the assembly and biosynthesis of pertussis toxin," Infect.Immun., 1990, vol. 56(6):1518-1526.
Alonso, Sylvie et al: "Production of nontypeable haemophilus influenzae HtrA by recombinant Bordetella pertussis with the use of filamentous hemagglutinin as a carrier," Infection and Immunity, 2005, pp. 4295-4301.
Abe, Takayuki et al: "Baculovirus induces an innate immune response and confers protection from lethal influenza virus infection in mice," J Immunol, 2003, vol. 171:1133-1139.
Feunou, Pascal et al: "Long-term immunity against pertussis induced by a single nasal administration of live attenuated B. pertussis BPZE1," Vaccine, 2010, vol. 28:7047-7053.
Mielcarek, Nathalie et al: "Dose Response of attenuated Bordetella pertussis BPZE1-induced protection in mice," Clinical and Vaccine Immunology, 2010, pp. 317-324.
Mielcarek, Nathalie et al: "Live attenuated B. pertussis as a single-dose nasal vaccine against whooping cough," PLoS Pathogens, 2006, vol. 2(7): 662-670.
Renauld-Mongenie, G. et al:Distinct roles of the N-terminal and C-terminal precursor domains in the biogenesis of the Bordetella pertussis filamentous hemagglutinin, J. Bacteriol., 1996, vol. 178(4):1053-1060.
Mattoo, S. et al: "Mechanisms of Bordetella pathogenesis," Frontiers in Bioscience, 2001, vol. 6:168-186.
Mattoo, S. and James D. Cherry: "Molecular pathogenesis, epidemiology, and clinical manifestations of respiratory infections due to *Bordetella pertussis* and other *Bordetella* subspecies," Clinical Microbiology Reviews, 2005, vol. 18(2):326-382.
Martignon, G. et al: "Does childhood immunization against infectious diseases protect from the development of atopic disease," Pediatr Allergy Immunol, 2005, vol. 16:193-200.
Locht, Camille et al: "Bordetella pertussis: from functional genomics to intranasal vaccination," Int. J. Med. Microbiol., 2004, vol. 293:583-588.
Harju, T.H. et al: Pathogenic bacteria and viruses in induced sputum or pharyngeal secretions of adults with stable asthma, Thorax, 2006, vol. 61:579-584.
Grueber, C. et al: "Early atopic disease and early childhood immunization—is there a link?," Allergy, 2008, vol. 63:1464-1472.
Gern, James E.: "Viral and bacterial infections in the development and progression of asthma," J Allergy Clin Immunol, 2000, pp: S497-S501.
Ennis, Darren P.: "A cellular pertussis vaccine protects against exacerbation of allergic asthma due to Bordetella pertussis in a murine model," Clin. Dagn. Lab. Immunol., 2005, vol. 12(3):409-417.
Kim, Young-Suk, et al.: "Inhibition of murine allergic airway disease by Bordetella pertussis," Immunology, 2004, vol. 112:624-630.
Li, R. et al: "Attenuated Bordetella pertussis BPZE1 protects against allergic airway inflammation and contact dermatitis in mouse models," Allergy, 2012, vol. 67:1250-1258.
Grueber, C. et al: "Common vaccine antigens inhibit allergen-induced sensitization and airway hyperresponsiveness in a murine model," Allergy, 2006, vol. 61:820-827.
Yusibov, V. et al.: "Peptide-based candidate vaccine against respiratory syncytial virus," Vaccine, 2005, vol. 23:2261-2265.
Walker, K. E. et al: "Characterizationof the dermonecrotic toxin in members of the genus *Bordetella*," Infect. Immun., 1994, vol. 62, No. 9:3817-3828.
Teman, UA. et al.: "A novel role for murine IL-4 in vivo: induction of MUC5AC gene expression and mucin hypersecretion," Am J Respir Cell Mol Biol., 1997, vol. 16(4):471-478.
Stith, Rebecca et al.: "The link between tracheal cytotoxin production and peptidoglycan recycling in Bordetella Pertussis," Abstracts of the General Meeting of the American Society for Microbiology, New Orleans; 1996; vol. 96:184 (XP008013937).
Li, Rui, et. al.: "Attenuated Bordetella pertussis BPZE1 as a live vehicle for heterologous vaccine antigens delivery thorugh the nasal route," Bioengineered Bugs, 2011, vol. 2(6):315-319.
Li, Rui, et al.: "Development of live attenuated Bordetella pertussis strains expressing the universal influenza vaccine candidate M2e," Vaccine, 2011, vol. 29:L5502-5511.
Romagnani, Sergio, "Immunologic influences on allergy and the TH1/TH2 balance," J Allergy Clin Immunol, 2004, pp. 395-400.
Nemery, B. et al.: "Interstitial lung disease induced by exogenous agents: factors governing susceptibility," Eur Respir J, 2001, vol. 18, Suppl. 32:30s-42s.
Neirynck, Sabine, et al.: "A universal influenza a vaccine based on the extracellular domain of the M2 protein," Nature Medicine, 1999, vol. 5:1157-1163.
Nagel, Gabriele et al.: "Association of pertussis and measles infections and immunizations with asthma and allergic sensitization in ISAAC Phase Two," Pediatric Allergy and Immunology, 2012, vol. 23:736-745.
Morokata, T. et al.: "C57BL/6 mice are more susceptible to antigen-induced pulmonary eosinophilia than BALB/c mice, irrespective of systemic T helper 1/T helper 2 responses," Immunology, 1999, vol. 98:345-351.
Mielcarek, Nathalie et al.: "Homologous and heterologous protection after single intranasal administration of live attenuated recombinant Bordetella pertussis," Nature Biotechnology, 1998, vol. 16:454-457.
Marsland, B.J., et al.: "Allergic airway inflammation is exacerbated during acute influenza infection and correlates with increased allergen presentation and recruitment of allergen-specific T-helper type 2 cells," Clinical & Experimental Allergy, 2004, vol. 34, Issue 8.
Mahon, B., et al.: "Atypical Disease after Bordetella pertussis Respiratory Infection of Mice with Targeted Disruptions of Interferon-γ Receptor or Immunoglobulin μ Chain Genes," J. Exp. Med., 1997, vol. 186, No. 11:1843-1851.
Locht, Camille, et al.: "Bordetella pertussis: from functional genomics to intranasal vaccination," Iny. J. Med. Microbiol., 2004, vol. 293:583-588.
Li, Z.M., et al.: "Cloning and sequencing of the structural gene for the porin protein of Bordetella pertussis," Molecular Biology, 1991, vol. 5 (7):1649-1656.
De Filette et al.: "Improved design and intranasal delivery of an M2e-based human influenza a vaccine," Vaccine, 2006, vol. 24, pp. 6597-6691.
Laemmli, U.K.: "Cleavage of Structural Proteins during the Assembly of the Head of Bacteriophage T4," Nature, 1970, pp. 680-685.
Humbert, Marc et al.: "Elevated expression of messenger ribonucleic acid encoding IL-13 in the bronchial mucosa of atopic and nonatopic subjects with asthma," Journal of Allergy and Clinical Immunology, 1997, vol. 99 (5):657-665.
Huang, Chin Chiang, et al.: "Experimental Whooping Cough," N Engl J Med, 1962, vol. 266:105-111.
Holgate, Stephen, et al.: "The anti-inflammatory effects of omalizumab confirm the central role of IgE in allergic inflammation," J Allergy Clin Immunol, 2005, vol. 115:459-465.
Hausman, Sally Z. and Burns, Drusilla L.: "Use of Pertussis Toxin Encoded by ptx Genes from *Bordetella* bronchiseptica to Model the Effects of Antigenic Drift of Pertussis Toxin on Antibody Neutralization."
Hansen, Gesine et al.: "Allergen-specific Th1 cells fail to counterbalance Th2 cell-induced airway hyperreactivity but cause severe airway inflammation," J. Clin. Invest., 1999, vol. 103:175-183.
Hamelmann, E. et al.: "Role of IgE in the development of allergic airway inflammation and airway hyperresponsiveness a murine model," Allergy, 1999, vol. 54:297-305.

(56) References Cited

OTHER PUBLICATIONS

Gleich, Gerald J.: "Mechanisms of eosinophil-associated inflammation," J. Allergy Clin. Immunol., 2000, pp. 651-663.
Giefing, Carmen et al.: "Discovery of a novel class of highly conserved vaccine antigens using genomic scale antigenic fingerprinting of pneumococcus with human antibodies," JEM, 2008, vol. 205(1):117-131.
Galli, Stephen J., et al.: "The development of allergic inflammation," Nature, 2008, vol. 454:445-454.
Zhao, Zhanqin, et al.: "Protecting mice from fatal Bordetella brochiseptica infection by immunization with recombinant pertactin antigens," Acta Microbiologica Sinica, 2008, vol. 48 (3):337-341.
Willems, Rob J.L. et al: "The efficacy of a whole cell pertussis vaccine and fimbriae against Bordetella pertussis and Bordetella parapertussis infections in a respiratory mouse model," Vaccine, 1998, vol. 16 (4)"410-416.
Varga, Steven M. et al: "The Attachment (G) Glycoprotein of Respiratory Syncytial Virus Contains a Single Immunodominant Epitope That Elicits Both Th1 and Th2 CD4+ T Responses," The Journal of Immunology, 2000, vol. 165:6487-6495.
Stibitz, Scott: "Use of conditionally counterselectable suicide vectors for allelic exchange," Methods in Enzymology, 1994, vol. 235:458-465; Abstract.
Stainer, D.W. and M.J. Scholte: "A simple chemically defined medium for the production of phase I Bordetella pertussis," Journal of General Microbiology, 1971, vol. 63:211-220.
Skerry, Ciaran M. and Bernard P. Mahon: "A live, attenuated bordetella pertussis vaccine provides long-term protection against virulent challenge in a murine model," Clinical and Vaccine Immunology, 2011, vol. 18:187-193.
Simon, R. et al: "A broad host range mobilization system for in vivo genetic engineering: transposon mutagenesis in gram negative bacteria," Nature Biotechnology, 1983, vol. 1:784-791.
Reveneau, Nathalie et al: "Tetanus toxin fragment C-specific priming by intranasal infection with recombinant Bordetella pertussis," Vaccine, 2002, vol. 20:926-933.
Renauld-Mongenie, Genevieve, et al: "Induction of mucosal immune responses against a heterologous antigen fused to filamentous hemagglutinin after intranasal immunization with recombinant Bordetella pertussis," Proc. Natl. Acad. Sci., 1996, vol. 93:7944-7949.
Quandt, J. and Michael F. Hynes: "Versatile suicide vectors which allow direct selection for gene replacement in gram-negative bacteria," Gene, 1993, vol. 127 (1):15-21; Abstract.
Power, Ultan F. et al: "Identification and characterisation of multiple linear B cell protectopes in the respiratory syncytial virus G protein," Vaccine, 2001, vol. 19, Issues 17-19:2345-2351; Abstract.
Feunou, Pascal: "T.119.T-but not B-cell-mediated protection induced by nasal administration using live attenuated bordetella pertussis BPZE1 Cross Protect Against B. Parapertussis," Clinical Immunology, 2009, vol. 131, Supplement 1, p. S86; Abstract.
Narasaraju, T. et al: "Adaptation of human influenza H3N2 virus in a mouse peumonitis model: insights into viral virulence, tissue tropism and host pathogenesis," Microbes and Infection 11, 2009:2-11.
Mutsch, M. et al: Use of the inactivated intranasal influenza vaccine and the risk of Bell's Palsy in Switzerland, The New England Journal of Medicine, 2004, vol. 350:896-903.
Mills, KH et al: "A respiratory challenge model for infection with Bordetella pertussis" application in the assessment of pertussis vaccine potency and in defining the mechanism of protective immunity, Dev Biol Stand, 1998, vol. 95:31-41; Abstract.
Mielcarek, Nathalie et al: "Attenuated bordetella pertussis: new live vaccines for intranasal immunisation," Vaccine, 2006, S2:54-55.
Mielcarek, Nathalie et al: "Intranasal priming with recombinant Bordetella pertussis for the induction of a systemic immune response against a heterologous antigen," Infection and Immunity, 1997:544-550.
Mielcarek, Nathalie et al: "Nasal vaccination using live bacterial vectors," Advanced Drug Delivery Review, 2001, vol. 51:55-69.
Mekseepralard, C. et al: "Protection of mice against human respiratory syncytial virus by wild-type and aglycosyl mouse-human chimaeric IgG antibodies to subgroup-conserved epitopes on the G glycoprotein," Journal of General Virology, 2006, vol. 87:1267-1273.
Menozzi, F.D. et al: "Identification and purification of transferring- and lactoferrin-binding proteins of bordetella pertussis and bordetella bronchiseptica," Infection and Immunity, 1991:3982-3988.
McGuirk, P. et al: Pathogen-specific T regulatory 1 cells induced in the respiratory tract by a bacterial molecule that stimulates interleukin 10 production by dendritic cells: a novel strategy for evasion of protective T helper type 1 resonses by Bordella pertussis.
Mascart, Francoise, et al: "Bordetella pertussis infection in 2-month-old infants promotes type 1 T cell responses," The Journal of Immunology, 2003, vol. 170:1504-1509.
Marsolais, David et al: "A critical role for the sphingosine analog AAL-R in dampening the cytokin response during infuenza virus infection," The National Academy of Sciences of the USA, 2009, vol. 106(5):1560-1565.
Feunou, Feunou, Pascal et al: "T- and B-Cell-Mediated Protection Induced by Novel, Live Attenuated Pertussis Vaccine in Mice. Cross Protection against Parapertussis," PLoS One, Apr. 2010, vol. 5, Issue 4:1-10.

* cited by examiner

Figure 1

SEQUENCE LISTING

<160> NUMBER OF SEQ ID NOS: 20

<210> SEQ ID NO 1
<211> LENGTH: 6
<212> TYPE: DNA
<213> ORGANISM: Artificial
<220> FEATURE:
<223> OTHER INFORMATION: XbaI site

<400> SEQUENCE: 1 tctaga 6

<210> SEQ ID NO 2
<211> LENGTH: 6
<212> TYPE: DNA
<213> ORGANISM: Artificial
<220> FEATURE:
<223> OTHER INFORMATION: XbaI site (with mutation)

<400> SEQUENCE: 2 tccaga 6

<210> SEQ ID NO 3
<211> LENGTH: 40
<212> TYPE: DNA
<213> ORGANISM: Artificial
<220> FEATURE:
<223> OTHER INFORMATION: Primer

<400> SEQUENCE: 3
gcatgcctgc aggtcgactc cagaggatcc ccgggtaccg 40

<210> SEQ ID NO 4
<211> LENGTH: 40
<212> TYPE: DNA
<213> ORGANISM: Artificial
<220> FEATURE:
<223> OTHER INFORMATION: Primer

<400> SEQUENCE: 4
cggtacccgg ggatcctctg gagtcgacct gcaggcatgc 40

<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
cttaagacgc gtcatatggg cggccgc 27

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
acgcgtgtgg aaactcctat ccg 23

<210> SEQ ID NO 7
<211> LENGTH: 36
<212> TYPE: DNA
<213> ORGANISM: Artificial
<220> FEATURE:
<223> OTHER INFORMATION: Primer

<400> SEQUENCE: 7
catatggccg ccagagccgc tatcagagct atcgtt 36

<210> SEQ ID NO 8
<211> LENGTH: 84
<212> TYPE: DNA
<213> ORGANISM: Artificial
<220> FEATURE:
<223> OTHER INFORMATION: Primer

<400> SEQUENCE: 8
ttcgtgccgt gctcgatctg ctcgaacaac ccgacctgct gggccatctg caagcgcatc 60
ccgaacaaga agccgggcaa gaag 84

<210> SEQ ID NO 9
<211> LENGTH: 66
<212> TYPE: DNA
<213> ORGANISM: Artificial
<220> FEATURE:
<223> OTHER INFORMATION: Primer

<400> SEQUENCE: 9
aggatccttc gtgccgtgct cgatctgctc gaacaacccg acctgctggg ccatctgcaa 60
gcgcat 66

<210> SEQ ID NO 10
<211> LENGTH: 69
<212> TYPE: DNA
<213> ORGANISM: Artificial
<220> FEATURE:
<223> OTHER INFORMATION: Primer

<400> SEQUENCE: 10
aggatccctt cttgcccggc ttcttgttcg ggatgcgctt gcagatggcc cagcaggtcg 60
ggttgttcg 69

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
aggatccttc gtgccgtgct cgatc 25

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
aggatccctt cttgcccggc ttctt 25

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
aacgcgtttc gtgccgtgct cgatc 25

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
acgcgtcttc ttgcccggct tctt 24

<210> SEQ ID NO 15
<211> LENGTH: 28
<212> TYPE: DNA
<213> ORGANISM: Artificial
<220> FEATURE:
<223> OTHER INFORMATION: Primer

<400> SEQUENCE: 15
catatgtgga cgaacttttg cacggaca 28

<210> SEQ ID NO 16
<211> LENGTH: 29
<212> TYPE: DNA
<213> ORGANISM: Artificial
<220> FEATURE:
<223> OTHER INFORMATION: Primer

<400> SEQUENCE: 16
acgcgtgaaa cgactgatga caaaattcg 29

<210> SEQ ID NO 17
<211> LENGTH: 27
<212> TYPE: PRT
<213> ORGANISM: Artificial
<220> FEATURE:
<223> OTHER INFORMATION: Peptide

<400> SEQUENCE: 17

```
Gly Gly Ser Leu Leu Thr Glu Val Glu Thr Pro Ile Arg Asn Glu Trp
1               5                   10                  15

Gly Ser Arg Ser Asn Asp Ser Ser Asp Gly Gly
            20                  25
```

```
<210> SEQ ID NO 18
<211> LENGTH: 32
<212> TYPE: PRT
<213> ORGANISM: Artificial
<220> FEATURE:
<223> OTHER INFORMATION: Peptide

<400> SEQUENCE: 18

Gly Gly Phe Val Pro Cys Ser Ile Cys Ser Asn Asn Pro Thr Cys Trp
1               5                   10                  15

Ala Ile Cys Lys Arg Ile Pro Asn Lys Lys Pro Gly Lys Lys Gly Gly
            20                  25                  30


<210> SEQ ID NO 19
<211> LENGTH: 30
<212> TYPE: DNA
<213> ORGANISM: Artificial
<220> FEATURE:
<223> OTHER INFORMATION: Primer

<400> SEQUENCE: 19

ccatgggtga aacgactgat gacaaaattg                                        30


<210> SEQ ID NO 20
<211> LENGTH: 42
<212> TYPE: DNA
<213> ORGANISM: Artificial
<220> FEATURE:
<223> OTHER INFORMATION: Primer

<400> SEQUENCE: 20

gcggccgcac gaacttttgc acggacaggt gctgctgcat ca                          42
```

RECOMBINANT *BORDETELLA* STRAINS

CROSS-REFERENCE TO RELATED APPLICATIONS

The present application is a continuation application under 35 U.S.C. §120 of copending International Patent Application Number. PCT/EP2013/071724, filed on Oct. 17, 2013, which designated the United States and claims the priority of European Patent Application Number 12306279.6, filed on Oct. 17, 2012.

STATEMENT AS TO FEDERALLY SPONSORED RESEARCH

Not applicable.

FIELD OF THE INVENTION

The invention relates to novel genetically attenuated *Bordetella pertussis* strains expressing a heterologous protein and their use as vaccines, namely for mucosal immunization.

The invention furthermore pertains to a method for increasing immunogenicity of a *Bordetella* strain.

BACKGROUND

Mucosal immunizations, such as nasal delivery of vaccines, have a number of advantages over classical parenteral vaccinations. They are needle-free, are less prone to contamination, depend less on trained medical or paramedical staff, may induce both systemic and mucosal immunity and are probably more suitable to protect against mucosal infections. However, most antigens are poor immunogens when given nasally and require the addition of potent mucosal adjuvants. One of the most potent mucosal adjuvant is cholera toxin or the closely related *Escherichia coli* heat-labile toxin and their detoxified derivatives. Unfortunately, the addition of this adjuvant to nasal vaccine formulations has been associated with Bell's palsy (Mutsch et al., 2004) and can therefore not be used in humans.

The authors of the present invention have recently developed an attenuated live nasal vaccine candidate against pertussis (Mielcarek et al., 2006), which has now successfully completed a first-in-man phase I safety trial (Thorstensson et al., in preparation). The concept of this candidate vaccine was based on the finding that natural infection with *Bordetella pertussis* via aerosol exposure is able to induce strong systemic B and T cell responses, even in very young infants (Mascart et al., 2003), as well as mucosal immunity. In addition, previous studies in non-human primates have led to the conclusion that "ultimate protection against whooping cough probably best follows a live *B. pertussis* inoculation" (Huang et al., 1962).

The *B. pertussis* strain was attenuated based on the knowledge of the molecular mechanism of *B. pertussis* virulence (Locht et al., 2001) and constructed by genetically inactivating pertussis toxin, by deleting the dermonecrotic toxin gene and by exchanging the ampG gene of *B. pertussis* by *Escherichia coli* ampG, thereby abolishing the production of the tracheal cytotoxin. In preclinical models, this vaccine candidate, named BPZE1, showed excellent safety (Mielcarek et al., 2006, 2010; Skerry et al., 2009; Kavanagh et al., 2010; Li et al., 2010) and induced fast, strong and long-lasting immunity upon a single nasal administration (Feunou et al., 2010).

Moreover, it was surprisingly uncovered that the BPZE1 strain, when nasally administered to mice was capable of eliciting a protective response against allergic and inflammatory conditions of the airways tract namely asthma and furthermore against topic allergies.

Reveneau et al. disclose a genetically attenuated *Bordetella* strain deficient in toxin production and expressing a hybrid protein comprising the N-terminal fragment of filamentous haemagglutinin (FHA) and protective tetanus toxin fragment C (TTFC), which strain does not produce mature FHA.

Coppens et al. disclose a genetically attenuated *Bordetella* strain deficient in toxin production and expressing a hybrid protein comprising the N-terminal fragment of filamentous haemagglutinin (FHA) and TbpB of *N. meningitis*, which strain does not produce mature FHA.

Alonso et al. discloses a genetically attenuated *Bordetella* strain deficient in toxin production and expressing a hybrid protein comprising the N-terminal fragment of filamentous haemagglutinin (FHA) and the HtrA protein of non typeable *Haemophilus influenza*, which strain does not produce mature FHA U.S. Pat. No. 6,841,358 discloses a genetically attenuated *Bordetella* strain deficient in toxin production and expressing a hybrid protein comprising the N-terminal fragment of filamentous haemagglutinin (FHA) and a model peptide of Sm28 GST of *Schistosoma mansoni*, which strain is deficient in the production of mature FHA However, the fhaB gene was not deleted for the purpose of increasing immunogenicity but the deletion was only coincidental and an intrinsic feature of the strain used as a carrier for the production of the heterologous antigen.

BPZE1 has subsequently been considered as a vector for the expression of heterologous protective antigens, in order to develop multivalent nasal vaccines able to protect simultaneously against several different pathogens. The neutralizing peptide SP70 from enterovirus 71 has been surface exposed and secreted by BPZE1 as a hybrid protein with filamentous haemagglutinin (FHA), and using the secretion machinery of FHA (Ho et al., 2008). Similarly, the FHA machinery was also used to secrete and expose the ectodomain of matrix protein 2 from the influenza A virus by BPZE1 (Li et al., 2011). Although systemic and local IgG and IgA responses could be elicited to the heterologous antigens upon administration of the recombinant BPZE1 derivatives, the immune responses to the passenger antigens were usually modest at best.

Upon trying to resolve the problem of poor immunogenicity obtained with the BPZE1 constructs, it was surprisingly discovered by the inventors that immunogenicity could be considerably increased when the native fhaB gene encoding the naturally occurring FHA protein was deleted or otherwise inactivated.

Moreover the strains thus obtained showed a substantially increased immunogenicity despite the anti-inflammatory properties of the native attenuated strain of *Bordetella pertussis* as evidenced by their activity against asthma and allergic diseases. Consequently the instant invention solves the problem for a vaccine for mucosal application, which is safe and capable of eliciting a potent immune response against an antigen present in a pathogen responsible for systemic or mucosal infections, including pathogens responsible for infections of the upper or lower respiratory tract.

SUMMARY

The invention provides a genetically attenuated recombinant *Bordetella pertussis* strain comprising a mutated pertussis toxin (ptx) gene, and a heterologous ampG gene and expressing a hybrid protein comprising the N-terminal fragment of filamentous haemagglutinin (FHA) and a heterologous epitope or antigenic protein or protein fragment, different from FHA, wherein the gene coding for the native FHA protein is inactivated.

The invention further provides a life attenuated vaccine for the treatment of a mucosal infectious disease comprising a *Bordetella pertussis* strain as defined above intended to elicit an immune response against a pathogen responsible for mucosal infections, namely of the upper or lower respiratory tract.

The present invention also relates to a method for prophylaxis of an infectious disease in a mammal, comprising administering to said mammal an effective amount of a vaccine comprising in a suitable vehicle a genetically attenuated recombinant *Bordetella pertussis* strain comprising a mutated pertussis toxin (ptx) gene, and a heterologous ampG gene expressing a fusion protein comprising the N-terminal fragment of filamentous haemagglutinin (FHA) and a heterologous epitope or antigenic protein or protein fragment, different from FHA, wherein the gene coding for the native FHA protein is inactivated.

In another aspect, the invention further provides methods for protecting a mammal against an infection by a pathogen infecting a mucosa, namely the lower or upper respiratory tract and/or eliciting an immune response against such a pathogen in a mammal using the composition or vaccine of the invention.

In still another aspect, the invention provides a method of eliciting an immune response against a pathogen with a mucosal tropism in a mammal, comprising: administering a recombinant attenuated *Bordetella pertussis* strain to the mammal, wherein the mutated *Bordetella pertussis* strain comprises a mutated pertussis toxin (ptx) gene, and a heterologous ampG gene and expresses a fusion protein comprising the N-terminal fragment of filamentous haemagglutinin (FHA) and a heterologous epitope or antigenic protein or protein fragment, different from FHA, of the pathogen against which the immune response is sought, wherein in said recombinant strain, the gene coding for the native FHA protein is inactivated.

In another aspect, the recombinant strain further comprises in addition to the mutated pertussis toxin (ptx) gene and the heterologous ampG gene, a deleted or mutated dermonecrotic toxin (dnt) gene. In some such aspects, the wild-type *Bordetella* strain ampG gene is replaced by an ampG gene of other Gram negative bacteria, such as an *E. coli* ampG gene.

In other aspects, the mutation of the ptx gene comprises the substitution of an amino acid involved in substrate binding and/or an amino acid involved in catalysis. In some such aspects, the substitution of the amino acid involved in substrate binding comprises R9K and the substitution of the amino acid involved in catalysis comprises E129G. In some aspects, the *Bordetella pertussis* strain comprises a triple mutant strain. In some such aspects, the *Bordetella* strain is the BPZE1 strain identified by accession number CNCM 1-3585.

In other aspects, the methods further comprise the prevention or treatment of the mucosal infection in the mammal. In some aspects, the *Bordetella pertussis* strain is administered prior to the mucosal infection. In some such aspects, the *Bordetella pertussis* strain is administered about 6 weeks or more prior to the mucosal infection. In other such aspects, the *Bordetella pertussis* strain is administered about 12 weeks or more prior to the mucosal infection. In some aspects, the pathogen responsible for the mucosal infection is the influenza virus, the respiratory syncytial virus or *Streptococcus pneumoniae*.

In some other aspects, the strain is administrated to a mammal in need of protective immunity against a mucosal infection. In some aspects the mammal is a human.

In still another aspect, the invention provides a method for enhancing the immune response toward a pathogen, in a mammal, comprising administering a vaccine based on a *Bordetella* recombinant vector, wherein said *Bordetella* expresses a fusion protein comprising the N-terminal fragment of filamentous haemagglutinin (FHA) and a heterologous epitope or antigenic protein or protein fragment of said pathogen against which the immune response is sought and wherein in said recombinant strain, the gene coding for the native FHA protein is inactivated.

The *Bordetella* strain is preferably a *Bordetella pertussis* strain, but may also be another *Bordetella* species, such as *Bordetella bronchispetica* or *Bordetella parapertussis*

The *Bordetella* strain comprises advantageously the features described above for BPZE1 and may be administered as a pharmaceutical or veterinary vaccine against a pathogen as described above.

The invention will be further illustrated by the following figures and examples. However, these examples and figures should not be interpreted in any way as limiting the scope of the present invention.

BRIEF DESCRIPTION OF THE DRAWINGS

FIG. 1. Serum anti-M2e IgG responses after administration of the indicated BPZE1 derivatives. BALB/c mice were i.n. immunized twice at a 4-week interval with $10^7$ CFU of the indicated strains. Phosphate-buffered saline (PBS)-vaccinated mice served as negative controls. Sera were collected two weeks after the last immunization, and serum IgG responses to M2e were measured by ELISA.

DETAILED DESCRIPTION

Figure 2:
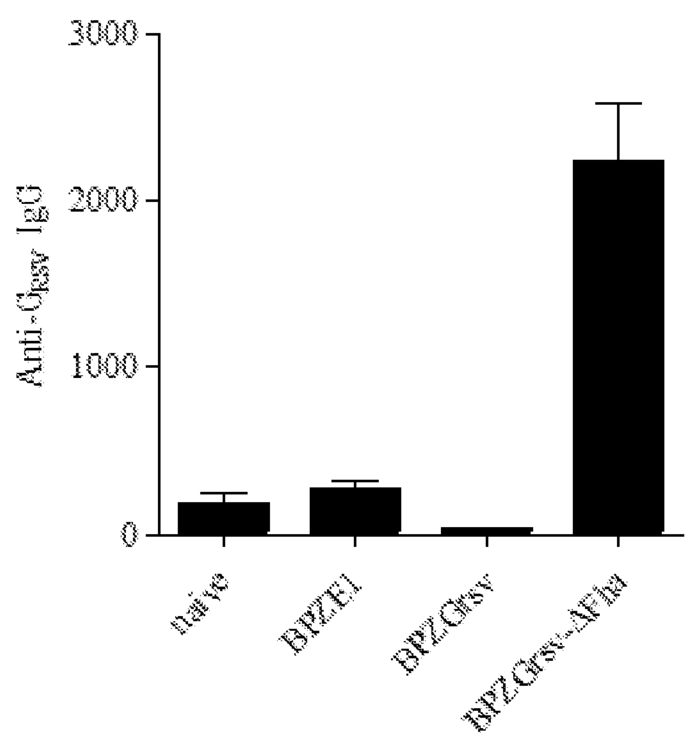
FIG. 2. Serum anti-$G_{RSV}$ IgG responses after administration of the indicated BPZE1 derivatives. BALB/c mice were i.n. immunized twice at a 4-week interval with $10^7$ CFU of the indicated strains. Phosphate-buffered saline-vaccinated mice (naïve) served as negative controls. Sera were collected two weeks after the last immunization, and serum IgG responses to $G_{RSV}$ were measured by ELISA.

Throughout the specification, several terms are employed and are defined in the following paragraphs.

As used herein, the abbreviation "PTX" refers to pertussis toxin, which is a secreted ADP-ribosylating toxin. PTX is comprised of five different subunits (named S1-S5) with each complex containing two copies of S4 and one copy of the other subunits. The subunits are arranged in an A-B structure. The A component is enzymatically active and is formed by the S1 subunit, while the B component is the receptor-binding portion and is made up of subunits S2-S5.

As used herein the abbreviation "DNT" refers to the *B. pertussis* dermonecrotic toxin, which is a heat labile toxin that can induce localized lesions in mice and other laboratory animals when it is injected intradermally.

As used herein the abbreviation "TCT" refers to tracheal cytotoxin, which is a virulence factor synthesized by *Bordetellae*. TCT is a peptidoglycan fragment and has the ability to induce interleukin-1 production and nitric oxide synthase. It has the ability to cause stasis of cilia and has lethal effects on respiratory epithelial cells.

As used herein the term "fusion protein" or "hybrid protein" refers to a protein comprising a first protein consisting of the N-terminal part of FHA and a second protein linked thereto wherein the second protein comprises a protein of *Bordetella* different from FHA or preferably a protein from a different species, namely a virus, fungus and bacterium responsible for a mucosal or systemic infection or a fragment of such a protein able to elicit an immune response against *Bordetella* or the species responsible for the mucosal or systemic infection.

The term "attenuated" refers to a weakened, less virulent *Bordetella pertussis* strain that is capable of stimulating an immune response and creating protective immunity, but does not in general cause illness.

"Treating" or "treatment" using the methods of the invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

The terms "protection" and "prevention" are used herein interchangeably and mean that an infection by a virulent pathogen is impeded.

The term "immunogenic composition" or "composition" means that the composition can induce an immune response and is therefore immunogenic. The term "immune response" means any reaction of the immune system. These reactions include the alteration in the activity of an organism's immune system in response to an antigen and can involve, for example, antibody production, induction of cell-mediated immunity, complement activation, development of immunological tolerance, development of immunological memory, or innate immune activation.

As used herein, the term "disease" has the meaning generally known and understood in the art and comprises any abnormal condition in the function or well being of a host individual. A diagnosis of a particular disease by a healthcare professional can be made by direct examination and/or consideration of results of one or more diagnostic tests.

The term "nasal administration" refers to any form of administration whereby an active ingredient is propelled or otherwise introduced into the nasal passages of a subject so that it contacts the respiratory epithelium of the nasal cavity. Nasal administration can also involve contacting the olfactory epithelium, which is located at the top of the nasal cavity between the central nasal septum and the lateral wall of each main nasal passage. The region of the nasal cavity immediately surrounding the olfactory epithelium is free of airflow. Thus, specialized methods must typically be employed to achieve significant absorption across the olfactory epithelium.

The term "aerosol" is used in its conventional sense as referring to very fine liquid droplets or solid particles carried by a propellant gas under pressure to a site of therapeutic application. A pharmaceutical aerosol of the invention contains a therapeutically active compound, which can be dissolved, suspended, or emulsified in a mixture of a fluid carrier and a propellant. The aerosol can be in the form of a solution, suspension, emulsion, powder, or semi-solid preparation. Aerosols of the invention are intended for administration as fine, solid particles or as liquid mists via the respiratory tract of a subject. Various types of propellants can be utilized including, but not limited to, hydrocarbons or other suitable gases. Aerosols of the invention can also be delivered with a nebulizer, which generates very fine liquid particles of substantially uniform size within a gas. Preferably, a liquid containing the active compound is dispersed as droplets, which can be carried by a current of air out of the nebulizer and into the respiratory tract of the patient.

The term "mammal" as used herein includes both humans and non-humans and includes but is not limited to humans, non-human primates, canines, felines, murines, bovines, equines, and porcines.

The term "therapeutically effective amount" is an amount that is effective to ameliorate a symptom of a disease. A therapeutically effective amount can be a "prophylactically effective amount" as prophylaxis can be considered therapy.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process or method. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

By "subject" it is meant a human. Typically the subject is a neonate, an infant or an adult.

As used in this specification and the appended claims, the singular forms "a", "an", and "the" include plural referents unless the content clearly dictates otherwise. Thus, for example, reference to "a vaccine" includes a combination of two or more vaccines, and the like.

The authors of the present invention have generated an optimized heterologous expression system for *Bordetella pertussis*, by using the N-terminal domain of FHA to carry heterologous antigens to the bacterial surface and into the extracellular milieu and by eliminating the original FHA-encoding gene. By using three different models (Influenza A Virus, Respiratory Syncytial Virus and *Streptococcus pneumoniae*), the invention provides the demonstration of a strong improvement in immunogenicity over previous systems.

The invention provides a recombinant attenuated *Bordetella pertussis* strain that can be used as an immunogenic composition or a vaccine to elicit an immune response in a mammal According to a first aspect, the invention provides a genetically attenuated *Bordetella pertussis* strain comprising a mutated pertussis toxin (ptx) gene, and a heterologous ampG gene and expressing a hybrid protein comprising the N-terminal fragment of filamentous haemagglutinin (FHA) and a heterologous epitope or antigenic protein or protein fragment, different from FHA, wherein the gene coding for the native FHA protein is inactivated.

Preferably the gene coding for the native FHA protein is inactivated by partial or fully deletion.

Preferably, the N-terminal fragment of the FHA protein comprises the amino acids from positions 1 to 862, more preferably from positions 1 to 330, starting with the first amino acid of the FhaB preprotein as defined by Lambert-Busine et al. (1998).

Life attenuated *B. pertussis* vaccines which are deficient for tracheal cytotoxin (TCT), active pertussis toxin (PTX), and dermonecrotic toxin (DNT) have been described in WO2007/104451 and in Mielcarek et al. (2006).

The *B. pertussis* ampG gene can be replaced by *E. coli* ampG. The resulting strain expressed less than 1% residual TCT activity. Any heterologous ampG gene from gram-negative bacteria that release very small amounts of peptidoglycan fragments into the medium, can be used in the present invention. Examples of suitable heterologous ampG gene include, but are not limited to ampG genes from *Escherichia coli, Salmonella, Enterobacteriaceae, Pseudomonas, Moraxella, Helicobacter, Stenotrophomonas, Legionella.*

PTX is a major virulence factor responsible for the systemic effects of *B. pertussis* infections and is composed of an enzymatically active moiety, called S1, and a moiety responsible for binding to target cell receptors. It is also one of the major protective antigens. The natural ptx genes can be replaced by a mutated version coding for an enzymatically inactive toxin. This can be achieved by replacing Arg-9 by Lys, and Glu-129 by Gly in S1, two key residues involved in substrate binding and catalysis, respectively. Allelic exchange can be used to first delete the ptx operon, and then to insert the mutated version.

The presence of the relevant toxin in the *B. pertussis* culture supernatants can be detected by immunoblot analysis.

Other mutations can also be made such as those described in U.S. Pat. No. 6,713,072, as well as any known or other mutations able to reduce the toxin activity to undetectable levels.

Allelic exchange can also be used to remove the dnt gene. Although the role of DNT in the virulence of *B. pertussis* is not certain, it has been identified as an important toxin in the closely related species *B. bronchiseptica* and displays lethal activity upon injection of minute quantities.

TCT is responsible for the destruction of ciliated cells in the trachea of infected hosts and may thus be involved in the cough syndrome. TCT is a breakdown product of peptidoglycan in the cell wall of Gram-negative bacteria, which generally internalize it into the cytosol by the AmpG transporter protein to be re-utilized during cell wall biosynthesis. B. *pertussis* AmpG is inefficient in the internalization of peptidoglycan breakdown products.

In a preferred embodiment, the life attenuated *B. pertussis* vaccine is the BPZE1 strain deposited with the Collection Nationale de Cultures de Microorganismes (CNCM, Institut Pasteur, 25 rue du Docteur Roux, F-75724 Paris Cedex 15, FRANCE) on Mar. 9, 2006 under the number CNCM 1-3585.

In one aspect, the recombinant *Bordetella* strain contains a mutated ptx gene, a deleted or mutated dnt gene, and a heterologous ampG gene. The heterologous ampG gene product can strongly reduce the amount of tracheal cytotoxin that is produced. The starting strain which is mutated can be any *Bordetella* strain including *B. pertussis, B. parapertussis*, and *B. bronchiseptica*. In one aspect the starting strain used to obtain the mutated *Bordetella* strain is *B. pertussis*. In another aspect, the strain is a triple mutant *Bordetella* strain. In another aspect, the *Bordetella* strain is identified by accession number CNCM 1-3585. In another aspect, the *Bordetella* strain is identified by accession number V09/009169.

The invention is not limited to only the mutants described above. Other additional mutations can be undertaken such as adenylate cyclase (AC) deficient mutants, lipopolysaccharide (LPS) deficient mutants, filamentous haemagglutinin (FHA), and any of the bvg-regulated components.

Advantageously the *Bordetella* strain has been made deficient in the production of toxins by elimination or deletion, at least partially, or by mutation, of the gene coding for the toxin so as to produce an inactive toxin or no toxin at all. Such a gene may be particularly the gene coding for *B. pertussis* toxin or any protein having a structure or function similarity with such a toxin. It can be also the gene coding for hemolysin/adenylate cyclase toxin or the dermonecrotic toxin expressed by *Bordetella* strains or for proteins having structure or function similarities. The *Bordetella* strain may be deficient in the production of one or more of these toxins.

The hybrid protein comprises part of the protein FHA and at least part of the protein of interest. This particular protein may be expressed by a strain of the *B. pertussis* species, such as the strain BPNX deposited under No. 1-1770 on Oct. 8, 1996, in the National Collection of Microorganism Cultures of Institut Pasteur, 28, Rue du Docteur Roux, F-75724, Paris, Cedex 15, France or the *B. pertussis* strain is identified by accession number CNCM 1-3585 or the *B. pertussis* strain is identified by accession number V09/009169.

Said hybrid protein may in particular be expressed by the mutated BPZE1 strain deposited with the Collection Nationale de Cultures de Microorganismes (CNCM) in Paris, France under the Budapest Treaty on Mar. 9, 2006 and assigned the number CNCM 1-3585.

A strain according to the present invention may be obtained by elimination of the gene of the toxin from the genome of a virulent strain expressing said hybrid protein, or by partial deletion or by mutation so as to produce an inactive toxin. Elimination may be carried out by any method known to those skilled in the art and particularly by crossing the virulent strain with a mobilizing strain, then by selecting, through markers adapted according to the strains, cells having lost the toxin gene. Such a loss of capacity of the virulent strain to express the toxin results from a double event of a homologous recombination between the virulent strain and a plasmid of the mobilizing strain. A person skilled in the art may refer for the obtaining of attenuated strains to the method described by Antoine and Locht (1990).

The characteristics of the deficient strains in the production of toxins, so selected, may be checked with various techniques, in particular by Western-blotting.

The avirulent strains expressing the hybrid protein may be obtained with the techniques known to those skilled in the art and, in particular, may be obtained as described in the above-mentioned French patent application FR-94 04 661 the contents of which are included into the present invention by reference. The recombinant DNAs comprising on the one hand a sequence coding for a heterologous peptide and on the other hand a sequence coding for a part of FHA are obtained through the methods known to those skilled in the art, in particular as described in Example V of the French patent application FR-94 04 661. This example results in the fusion of the region 190-211 of glutathion-S-transferase of 28 kDa (Sm28GST) of *Schistosoma mansoni*, with the truncated FHA protein. The recombinant DNAs coding for the hybrid proteins are selected, the sequence thereof is checked according to methods known to those skilled in the art, then transferred into *Bordetella* cells.

The person skilled in the art may refer for the implementation of the present invention to general manuals relating to these techniques and in particular to the following manual: Maniatis et al., 1982, Molecular Cloning: Laboratory Manual, Cold Spring Harbor Laboratory, Cold Spring Harbor N.Y., USA, or one of its recent re-editions.

The heterologous protein, the sequence of which is included into the hybrid protein, may be any antigenic protein sequence, especially *Bordetella, Streptococcus, Shigella, Neisseria, Haemophilus, Moraxella, Vibrio, Escherichia, Borrellia, Mycobacterium* antigens, diphtheria, tetanus or cholera toxins or toxoids, viral antigens including influenza, RSV, hepatitis B, hepatitis C, poliovirus, rhinovirus or HIV, or parasitic antigens such as those of *Plasmodium, Schistosoma* or *Toxoplama*. It may also include an epitope of a protein capable of being expressed by pathogens upon mucosal infections or systemic infections.

Advantageously, the heterologous protein is all or part of the M2 matrix protein of the influenza A virus.

In a preferred embodiment of the invention, the heterologous protein is the extracellular domain of the M2 protein.

In another embodiment, the heterologous protein is all or part of the G protein of RSV, namely the portion extending from amino-acid residues 170 to 197, containing both B and T cell epitopes (Yusibov et al., 2005; Varga et al., 2000).

In still another embodiment, the heterologous protein is all or part of the PcsB protein, a broadly cross-reactive vaccine antigen of *S. pneumonia* (Giefing et al., 2008)

The construction of a mutated *Bordetella* strain of the invention may begin with replacing the *Bordetella* ampG gene in the strain with a heterologous ampG gene. Any heterologous ampG gene known in the art can be used in the invention. Examples of these can include all gram-negative bacteria that release very small amounts of peptidoglycan fragments into the medium per generation. Examples of gram-negative bacteria include, but are not limited to: *Escherichia coli, Salmonella, Enterobacteriaceae, Pseudomonas, Moraxella, Helicobacter, Stenotrophomonas, Legionella*, and the like. Typically, by replacing the *Bordetella* ampG gene with a heterologous ampG gene, the amount of tracheal cytoxin (TCT) produced in the resulting strain expresses less than 1% residual TCT activity. In another aspect, the amount of TCT toxin expressed by the resulting strain is between about 0.6% to 1% residual TCT activity or about 0.4% to 3% residual TCT activity or about 0.3% to 5% residual TCT activity.

PTX is a major virulence factor responsible for the systemic effects of *B. pertussis* infections, as well as one of the major protective antigens. Due to its properties, the natural ptx gene can be replaced by a mutated version so that the enzymatically active moiety S1 is replaced by an enzymatically inactive subunit, but the immunogenic properties of the pertussis toxin are not affected. This can be accomplished by replacing the arginine (Arg) at position 9 of the sequence with a lysine (Lys) (R9K). Furthermore, a glutamic acid (Glu) at position 129 can be replaced with a glycine (Gly) (E129G). These amino acid positions are involved in substrate binding and catalysis, respectively. In other aspects, other mutations can also be made such as those described in U.S. Pat. No. 6,713,072, incorporated herein by reference, as well as any known or other mutations able to reduce the toxin activity. In one aspect, allelic exchange can first be used to delete the ptx operon and then to insert a mutated version.

In another aspect of the invention, the dnt gene can be removed from the *Bordetella* strain using allelic exchange. Besides the total removal, the enzymatic activity can also be inhibited by a point mutation. Since DNT is constituted by a receptor-binding domain in the N-terminal region and a catalytic domain in the C-terminal part, a point mutation in the dnt gene to replace Cys-1305 to Ala-1305 inhibits the enzyme activity of DNT (Kashimoto et al., 1999).

The transgene coding for the hybrid protein may be inserted into the mutated strain defined above by insertion of a genetic sequence or plasmid by using procedures well known in the art.

Advantageously, the gene coding the heterologous protein or epitopic fragment thereof is fused as a single or multiple copies to the coding sequence of the N-terminal part of FHA.

The transgene is advantageously inserted into the dnt locus of *B. pertussis*, by allelic exchange using plasmids containing up- and downstream regions of the dnt gene as described by Mielcarek et al. (2006) for the deletion of the dnt gene.

The recombinant *Bordetella* strains of the invention can be used in immunogenic compositions for the treatment or prevention of mucosal infections. Such immunogenic compositions are useful to raise an immune response, either an antibody response and or a T cell response in mammals. For example, the T cell or antibody response can be such that it protects a mammal against influenza, RSV, *S. pneumonaie* or other infections or against their consequences/diseases/symptoms.

The mutated *Bordetella* strains of the invention can be used in vaccines or immunogenic compositions. In one aspect, the strains are used for nasal administration.

Compositions of the invention may be administered in conjunction with other immunoregulatory agents, including adjuvants although the addition of an adjuvant is not preferred.

In another aspect, the invention further provides methods for protecting a mammal against an infection by a pathogen infecting a mucosa, namely the lower or upper respiratory tract and/or eliciting an immune response against such a pathogen in a mammal using the composition or vaccine of the invention.

In still another aspect, the invention provides a method of eliciting an immune response against a pathogen with a mucosal tropism in a mammal, comprising: administering a recombinant *Bordetella pertussis* strain comprising a mutated pertussis toxin (ptx) gene, and a heterologous ampG gene and expressing a hybrid protein comprising the N-terminal fragment of filamentous haemagglutinin (FHA) and a heterologous epitope or antigenic protein or protein fragment, different from FHA, wherein the gene coding for the native FHA protein is inactivated In one aspect, the recombinant strain comprises a mutated pertussis toxin (ptx) gene, a deleted or mutated dermonecrotic (dnt) gene, and a heterologous ampG gene In some such aspects, the wild-type *Bordetella* strain ampG gene is replaced by an ampG gene of other Gram negative bacteria, such as an *E. coli* ampG gene.

In other aspects, the mutation of the ptx gene comprises the substitution of an amino acid involved in substrate binding and/or an amino acid involved in catalysis. In some such aspects, the substitution of the amino acid involved in substrate binding comprises R9K and the substitution of the amino acid involved in catalysis comprises E129G. In some aspects, the *Bordetella* strain comprises a triple mutant strain. In some such aspects, the *Bordetella* strain is the BPZE1 strain identified by accession number CNCM 1-3585.

In other aspects, the methods further comprise the prevention or treatment of the mucosal infection in a mammal. In some aspects, the *Bordetella* strain is administered prior to the mucosal infection. In some such aspects, the *Bordetella* strain is administered about 6 weeks or more prior to the mucosal infection. In other such aspects, the *Bordetella* strain is administered about 12 weeks or more prior to the mucosal infection. In some aspects, the pathogen responsible for the mucosal infection is the influenza virus, the respiratory syncytial virus or *Streptococcus pneumoniae*.

In some other aspects, the strain is administrated to a mammal in need of protective immunity against a mucosal or systemic infection. In some aspects the mammal is a human.

Methods for treatment or prevention of diseases related to mucosal or systemic infections include administering a therapeutically effective amount of a composition of the invention. The composition of the invention can be formulated in pharmaceutical compositions. These compositions can comprise, in addition to one or more of the strains, a pharmaceutically acceptable excipient, carrier, buffer, stabilizer, or other materials well known to those skilled in the art. Such materials should typically be non-toxic and should not typically interfere with the efficacy of the active ingredient.

The composition can typically be used to elicit mucosal immunity. In other aspects, the number of bacteria in each dosage is adjusted to attain an effective immune response in a mammal. The number of bacteria or cfus in each dosage can be about 1, 10, 100, 1000, 10000, 100000, 1000000, $5*10^6$, $10^7$, $10^8$ or more or any dosage between said each dosage.

Formulation of the vaccines of the present invention can be accomplished using art recognized methods. The amount of vaccines of the invention to be administered to a subject and the regime of administration can be determined in accordance with standard techniques well known to those of ordinary skill in the pharmaceutical and veterinary arts taking into consideration such factors as the adjuvant (if present), the age, sex, weight, species and condition of the particular subject and the route of administration. The administration of the vaccine is usually in a single dose. Alternatively, the administration of the vaccine of the invention is made a first time (initial vaccination), followed by at least one recall (subsequent administration), with the vaccine.

Typically the vaccines can be administered by nasal administration or by inhalation. This type of administration is low in costs and enables the colonization by the life attenuated *B. pertussis* vaccine of the invention of the respiratory tract. Nasal administration may be accomplished with a life attenuated *B. pertussis* vaccine under the form of liquid solution, suspension, emulsion. Solutions and suspensions are administered as drops. Solutions can also be administered as a fine mist from a nasal spray bottle or from a nasal inhaler. Gels are dispensed in small syringes containing the required dosage for one application. Inhalation may be accomplished with a life attenuated *B. pertussis* vaccine under the form of solutions, suspensions, and powders; these formulations are administered via an aerosol, droplets or a dry powder inhaler. The powders may be administered with insufflators or puffers.

Of the various mucosal delivery options available, the intranasal route is the most practical as it offers easy access with relatively simple devices that have already been mass produced. The composition of the invention is thus preferably adapted for and/or packaged for intranasal administration, such as by nasal spray, nasal drops, gel or powder.

Whatever the route of delivery, compositions of the invention are preferably packaged in unit dose form. Effective doses can be routinely established. A typical human dose of the composition for injection or for intranasal use has a volume between 0.1-1.0 ml e. g. two 500 μl sprays, one per nostril.

Compositions of the invention are preferably buffered e. g. at between pH 6 and pH 8, generally around pH 7.

EXAMPLES

Material & Methods

Bacterial Strains and growth conditions. The *B. pertussis* strains used for this study are listed in Table 1. They were grown on Bordet-Gengou agar (Difco, Detroit, Mich.) supplemented with 1% glycerol, 20% defibrinated sheep blood, and 100 μg/ml streptomycin (Sigma Chemical Co., St Louis, Mo.) at 37° C. for 72 h. Liquid cultures of *B. pertussis* were incubated as described previously (Menozzi et al., 1991) in Stainer-Scholte medium (Stainer and Scholte, 1970) containing 1 g/liter heptakis (2,6-di-o-methyl) β-cyclodextrin (Sigma).

Construction of plasmids and recombinant BPZE1 strains. The different BPZE1 derivatives described here all contained the transgene in the dnt locus of BPZE1 inserted by allelic exchange, using plasmids derived from pJQmp200rpsL12 (Quandt & Hynes, 1993) and containing up- and downstream regions of the dnt gene, as described by (Mielcarek et al. 2006) for the deletion of the dnt gene in BPZE1.

Construction of pXR1. First, the XbaI site of the backbone of this plasmid (Mielcarek et al., 2006), named pJQdntUPLO, was changed from TCTAGA (SEQ ID NO: 1) to TCCAGA (SEQ ID NO: 2) by using the primers SP Xba mut 5'-GCATGCCTGCAGGTCGACTCCAGAGGATCCCCGGGTACCG-3' (SEQ ID NO: 3) and ASP Xba mut 5'-CGGTACCCGGGGATCCTCTGGAGTCGACCTGCAGGCATGC-3' (SEQ ID NO: 4) and QuickChangeII® XL (Stratagen) according to manufacturer's specifications. The dnt upstream and the dnt downstream regions of the resulting plasmid, named pXR1, were sequenced. One mutation G→A in the dnt downstream region (corresponding to position 3,651,839 of the *B. pertussis* genome, GenBank NC-002929.2) was noticed.

Construction of pXR1-Fha44 A synthetic gene coding for the 5' part of the fhaB gene was purchased from Eurogentec (Liege, Belgium). This gene, named fha44c, contains 2,583 by coding for amino acids 1 to 861 of FhaB, the precursor of FHA (from nucleotide position 253 to 2,835, GenBank M60351.1), except for four silent changes (G354C, C864G, G2,331C and A2,556G), a 27-bp multiple cloning site with the sequence 5'-CTTAAGACGCGTCATATGGGCGGCCGC-3' (SEQ ID NO: 5) and two TGA termination codons.

This sequence was provided in a plasmid named pUC57-Fha44$_c$. This plasmid was digested with XhoI and XbaI, and the fragment corresponding to fha44c was inserted into XhoI/XbaI-digested pXR1. The resulting plasmid, pXR1-Fha44, contains thus the 813-bp region upstream of the ATG start codon of the dnt gene (from position 3,646,310 to position 3,647,122 of the *B. pertussis* genome, GenBank NC-002929.2), the region coding for the carrier protein Fha44 fused to the 27-bp multiple cloning site, followed by two TGA termination codons the 83-pb region downstream of the TGA termination codon of the dnt gene (from position 3,651,479 to position 3,651,564 of the *B. pertussis* genome, GenBank NC-002929.2), a XbaI restriction site and the 712-pb dnt downstream region of pXR1 (identical to the sequence from position 3,651,565 to position 3,652,276 of the *B. pertussis* genome, GenBank NC-002929.2, except for the G→A mutation corresponding to position 3,651,839 of the *B. pertussis* genome, GenBank NC-002929.2 that was present in pXR1). The plasmid was sequenced to confirm the absence of unexpected mutations.

Construction of BPZE1 derivatives expressing Fha44-M2e. The sequence coding for 3 copies of the M2e peptide was amplified by PCR from pGA4-3M2e (from Geneart AG), containing the coding information for three tandem copies of M2e. Each M2e copy in pGA4-3M2e is separated by a 9 amino acid peptide and cysteine codons at positions 17 and 19 in M2e were replaced by serine. Oligonucleotides 5'-ACGCGTGTGGAAACTCCTATCCG-3' (SEQ ID NO: 6) and 5'-CATATGGCCGCCAGAGCCGCTATCAGAGCTATCGTT-3' (SEQ ID NO: 7) were used as primers. The amplified DNA fragment was then inserted into pCRII-TOPO (Invitrogen) and verified by DNA sequencing. A 273-bp fragment obtained after MluI/NdeI digestion was cloned into the MluI/NdeI sites of pXR1-Fha44 to yield pHKG3. This plasmid was sequenced to verify the absence of unwanted alterations and was introduced into *E. coli* SM10 (Simon et al., 1983) by transformation, and the resulting recombinant *E. coli* SM10 bacteria were conjugated with BPZE1. Two successive homologous recombination events were selected as described (Stibitz, 1994). The recombinant strains were then analyzed by PCR to identify clones in which the hybrid gene was correctly inserted into the dnt locus. The recombinant BPZE1 strain was named BPZM2e.

To construct BPZEM2e-ΔFha, a FHA-deficient recombinant strain, the FHA-encoding gene was inactivated in BPZM2e using the integration vector pFUS2 as previously described (Antoine et al., 2000).

Construction of BPZE1 derivatives expressing Fha44-G$_{RSV}$. The oligonucleotide coding for amino acids 170 to 197 of the glycoprotein of RSV strain A2 (GenBank AAC55969.1) was synthesized according to the *B. pertussis* codon usage and had the following sequence:

```
                                        (SEQ ID NO: 8)
5'-TTCGTGCCGTGCTCGATCTGCTCGAACAACCCGACCTGCTGGGCCAT

CTGCAAGCGCATCCCGAACAAGAAGCCGGGCAAGAAG-3'.
```

It was produced by PCR using 100 nM of overlapping oligonucleotides.

5'-AGGATCCTTCGTGCCGTGCTCGATCTGCTCGAACAACCCGACCTGCT GGGCCATCTGCAAGCGCAT-3' (SEQ ID NO: 9) and 5'-AGGATCCCTTCTTGCCCGGCTTCTTGTTCGGGATGCGCTTGCAGATG GCCCAGCAGGTCGGGTTGTTCG-3' (SEQ ID NO: 10) as template and 400 nM oligonucleotides

```
5'-AGGATCCTTCGTGCCGTGCTCGATC-3' (SEQ ID NO: 11)
and

5'-AGGATCCCTTCTTGCCCGGCTTCTT-3' (SEQ ID NO: 12)
as primers.
```

The resulting 96-bp fragment was then inserted into pCRII-TOPO (Invitrogen), yielding pCRII-TOPO-G$_{RSV}$-BamHI, and was sequenced to confirm the absence of unexpected mutations. The RSV G sequence was then amplified by PCR, using pCRII-TOPO-G$_{RSV}$BamHI as template and oligonucleotides

```
5'-AACGCGTTTCGTGCCGTGCTCGATC-3' (SEQ ID NO: 13)
and

5'-ACGCGTCTTCTTGCCCGGCTTCTT-3'  (SEQ ID NO: 14)
as primers.
```

The resulting 96-bp fragment was then inserted into pCRII-TOPO, yielding pCRII-TOPO-G$_{RSV}$MluI and was sequenced to confirm the absence of unexpected mutations. pCRII-TOPO-G$_{RSV}$MluI was digested with MluI, and the RSV G sequence was inserted into MluI-digested pXR1-Fha44 to yield pXR1-Fha44/G$_{RSV}$. This plasmid was sequenced to verify proper orientation of the insert and the absence of unwanted alterations, and it was then introduced into *E. coli* SM10 (Simon et al., 1983) by transformation, and the resulting recombinant *E. coli* SM10 bacteria were conjugated with BPZE1. Two successive homologous recombination events were selected as described (Stibitz, 1994). The recombinant strains were then analyzed by PCR to identify clones in which the hybrid gene was correctly inserted into the dnt locus. The recombinant BPZE1 strain was named BPZG$_{RSV}$.

To construct BPZG$_{RSV}$-ΔFha, a FHA-deficient recombinant strain, the FHA-encoding gene was inactivated in BPZG$_{RSV}$ using the integration vector pFUS2 as previously described (Antoine et al., 2000).

Construction of BPZE1 derivatives expressing Fha44-PcsB. The coding sequence of the mature form of PcsB (from amino acid residue 28 to residue 278) was amplified by PCR using the chromosomal DNA from *S. pneumoniae* serotype 1 (clinical isolate E1586) as template and synthetic oligonucleotides SP-PcsB 5'-CATATGTGGACGAACTTTTGCACGGACA-3' (SEQ ID NO: 15) and ASP-PcsB 5'-ACGCGTGAAACGACTGATGACAAAATTCG-3' (SEQ ID NO: 16) as primers. *S. pneumoniae* was boiled and 10 μM of the oligonicleotides were added in the PCR mixture. The resulting 750-bp fragment was inserted into pCRII-TOPO, yielding pCRII-TOPO-PcsB, and then sequenced. pCRII-TOPO-PcsB was digested with MluI and NdeI, and the fragment corresponding to the PscB sequence was inserted into MluI/NdeI-digested pXR1-Fha44, yielding pXR1-Fha44-PcsB. After sequencing this plasmid was introduced into *E. coli* SM10 (Simon et al., 1983) by transformation, and the resulting recombinant *E. coli* SM10 bacteria were conjugated with BPZE1. Two successive homologous recombination events were selected as described (Stibitz, 1994). The recombinant strains were then analyzed by PCR to identify clones in which the hybrid gene was correctly inserted into the dnt locus. The recombinant BPZE1 strain was named BPZPcsB.

To construct BPZPcsB-ΔFha, a FHA-deficient recombinant strain, the FHA-encoding gene was inactivated in BPZM2e using the integration vector pFUS2 as previously described (Antoine et al., 2000).

Protein analysis and immunodetection of the recombinant chimeric proteins. For the detection of the Fha44-3M2e, the Fha44-$G_{RSV}$ and the Fha44-PcsB chimeric proteins, the recombinant strains were grown for 48 hours in 10 ml Stainer-Scholte medium supplemented with 100 μg/ml Streptomycin. The cells were then centrifuged for 15 minutes at 4,000×g. 400 μl supernatant was collected, and the cells were resuspended in 400 μl PBS. 200 μl of 3×Laemmli (1970) loading buffer was added to the supernatants and to the cell suspensions. The mixtures were then heated at 95° C. for 10 min. The chromosomal DNA was sheared by passing the bacterial suspension 10 times through a 27-gauge needle. This was followed by heating at 95° C. for 15 min. 10 μl of each sample was loaded onto a 10% sodium dodecyl sulfate-polyacrylamide gel electrophoresis gel (SDS-PAGE) for Immunoblot analysis or Coomassie-blue staining. A non-recombinant BPZE1 supernatant and/or whole cell lysate was used as negative controls.

After electrophoresis, the proteins were electrotransferred onto nitrocellulose membranes and incubated with the mouse anti-M2e (Neirynck et al., 1999) or anti-$G_{RSV}$ (Mekseepralard et al., 2006) antibodies in PBS containing 0.1% Tween 20 and 1% bovine serum albumin. Alkaline phosphatase-conjugated goat anti-mouse monoclonal antibodies (Promega) diluted 1:4,000 were used for chromogenic detection of the proteins by the addition of the alkaline phosphatase substrate (nitroblue tetrazolium and 5-bromo-4-chloro-3-indolylphosphate reagents; Promega). The sizes of the reactive bands were determined from the migration distance of the All Blue protein Marker (Biorad).

Mouse colonisation and immunogenicity. BALB/c mice were obtained from Charles River (l'Abresle, France) and maintained under specific pathogen-free conditions in the animal facilities of the Institut Pasteur de Lille. For lung colonization, 6-weeks old BALB/c mice were lightly sedated by intraperitoneal (i.p.) injection of an anesthetic cocktail (ketamine+atropine+valium) and intranasally (i.n.) immunized with 20 μl PBS containing $10^6$ or $10^7$ colony-forming units (CFU) of BPZE1 or recombinant strains as previously described (Mielcarek et al., 2006). The mice were sacrificed at indicated time points after i.n. administration, and their lungs were harvested, homogenized in PBS and plated in serial dilutions onto BG-blood agar to count CFUs after incubation at 37° C. for three to four days, as described (Mielcarek et al., 2006).

For immunization studies, groups of 6-weeks old BALB/c mice were immunized i.n. with 20 μl PBS containing $10^7$ CFU of BPZE1 or recombinant strains, and then boosted at 4 week intervals with the same amount of bacteria.

Antibody detection. 96-well plates were coated with 2 μg/ml of the synthetic M2e peptide (Ac-GGSLLTEVETPIRNEWGSRSNDSSDGG-NH2, SEQ ID NO: 17), with 2 μg/ml of the synthetic $G_{RSV}$ peptide (Ac-GGFVPCSICSNNPTCWAICKRIPNKKPGKKGG-NH2, SEQ ID NO: 18) or 2 μg/ml of recombinant PcsB, incubated overnight at 4° C. and washed with PBS containing 0.05% Tween-20 (PBST). Subsequently, the plates were blocked with 100 μl/well of blocking buffer (2% BSA in PBST) for 1 h at 37° C. After three washes, 100 μl of serially diluted sera was added to the wells and incubated for 2 h at 37° C. After three additional washes, the plates were incubated for 1 h at 37° C. with 100 μl of horseradish-peroxidase (HRP)-labeled anti-mouse IgG (Southern Biotech) diluted 1:4000 in PBST. Following five washes, the plates were incubated with 100 μl of HRP substrate TMB solution (Interchim) for 30 min at room temperature. The reaction was stopped by the addition of 50 μl of 1 M $H_3PO_4$. The optical density (OD) was measured with a Biokinetic reader EL/340 microplate at 450 nm. The end titer was determined as the highest serum dilution that had an optical density reading more than twice that of the negative control serum.

Production of recombinant PcsB. The PcsB fragment was amplified by PCR using the chromosomal DNA from *S. pneumoniae* serotype 1 (clinical isolate E1586) as template and synthetic oligonucleotides SP-PcsBexp 5'-CCATGGGTGAAACGACTGATGACAAAATTG-3' (SEQ ID NO: 19) and ASP-PcsBexp 5'-GCGGCCGCACGAACTTTTGCACGGACAGGTGCTGCTGCATCA-3 (SEQ ID NO: 20). The amplicon was inserted into pCRII-TOPO (Invitrogen, Cergy-Pontoise, France) and sequenced, yielding pCRII-TOPOPcsBexp. The NotI/NcoI fragment of this vector was inserted into pET24D+, yielding pET24DPcsB. This plasmid was introduced into *E. coli* BL21 for production and purification of PcsB. The recombinant bacteria were grown at 37° C. in liquid LB broth supplemented with kanamycin (25 μg/ml). When the OD600 had reached 0.8, expression was induced by the addition of 1 mM Isopropyl-d-thiogalactopyranoside (IPTG) for 4 h at 37° C. The induced cells were then harvested by centrifugation at 8,000 rpm for 20 min at 4° C. and were suspended in lysis buffer A (PBS, pH 7.0; 350 mM NaCl; 10% glycerol) supplemented with 1 tablet/25 ml protease inhibitors [complete TM, EDTA free (Roche Molecular Biochemicals, Meylan, France)].

Cells were broken by two passages through a French pressure cell. After harvesting the membrane fractions by centrifugation (15,000 rpm for 20 min), the supernatant of the cell lysate was passed through the nickel-NTA agarose (Qiagen) (Chelating Sepharose, Fast flow, with Ni2+ metal coupled, Amersham-Pharmacia) at a flow rate of 0.5 ml/min. The unbound material was washed with buffer A until the OD reached the baseline. Elution of the bound histidine-tagged protein was carried out using a step-wise gradient with 15 ml buffer A containing 50 mM, 100 mM or 200 mM imidazole. The eluates were collected as 2-ml fractions. The samples obtained were then analyzed by SDS-PAGE using a 12% polyacrylamide gel and Coomassie-blue staining, and the fractions containing PcsB protein were pooled and dialyzed overnight against PBS at 4° C. Protein concentrations were estimated using the BCA test (Pierce), using the manufacturer's instructions.

RESULTS

1. Recombinant BPZE1 Strain Producing Fh44-3M2e (BPZM2e)

Construction of Recombinant BPZE1 Strain Producing Fha44-3M2e (BPZM2e)

The extracellular domain of matrix protein M2 (M2e) of the influenza A virus has been proposed as a universal protective antigen against influenza (Neirynck et al., 1999; de Filette et al., 2006). To express M2e in BPZE1, we have used Fha44 as carrier. Fha44 is the 80-kDa N-terminal fragment of FHA and is better secreted by *B. pertussis* than full-length FHA (Renauld-Mongénie et al., 1996).

Three copies of the M2e-encoding sequence were fused to the Fha44-encoding sequence. The construct was inserted into the BPZE1 chromosome at the dnt locus by allelic exchange, placing the transgene under the control of the dnt promoter in the recombinant strain named BPZM2e.

Unconcentrated culture supernatant and whole cell extracts of BPZE1 and BPZM2e were examined by immunoblot analysis using an anti-M2e monoclonal antibody. A 94-kDa band, corresponding to the expected size of the Fha44-3M2e chimeric protein, was detected in the culture supernatant of the recombinant strain. A similar size protein also reactive with the anti-M2e antibody was also detected in the whole cell extracts. This observation indicates that the chimeric protein was secreted from the recombinant strain and was also associated with bacterial cell of BPZM2e.

Lung Colonization and Immunogenicity of BPZM2e

First the growth kinetics of BPZM2e in vitro in Stainer Scholte medium was compared to that of the parent strain BPZE1. There was no statistical difference between the two strains, indicating that the general bacterial fitness was not impaired by the expression of Fha44-3M2e.

To study the ability of the recombinant strain BPZM2e to colonize the murine respiratory tract, BALB/c mice were infected i.n. with $10^6$ CFU of BPZM2e or with non-recombinant BPZE1, and their colonization profiles were compared. The colonization profile of recombinant strain BPZM2e was indistinguishable from that of the corresponding parental strain BPZE1, indicating that the insertion of Fha44-3M2e does not alter the ability of the bacteria to colonize the lungs of mice.

The antibody responses to the M2e peptide were examined by ELISA at different time points after administration of BPZM2e. However, no M2e-specific antibodies were detected at any time point. The BPZM2e dose was then increased ten-fold, and BALB/c mice were i.n. immunized twice at a 4-week interval with $10^7$ CFU of BPZE1 or recombinant BPZM2e. Sera were collected at 2 weeks and 4 weeks after the first immunization, and 2 weeks after the last immunization to evaluate the systemic anti-M2e IgG. Again, no significant antibody response to M2e was detected in sera.

Mutation of FHA and Characterization of the New Recombinant Strain (BPZM2e-ΔFHA)

The chromosomal gene coding for FHA (fhaB) was then inactivated from BPZM2e by introducing a pFus2 derivative that contains an internal fragment of fhaB (Antoine et al., 2000). As pFus2 is not able to replicate in *B. pertussis*, the integration of the plasmid into the fhaB gene is forced by homologous recombination, thereby interrupting this gene. The integrants were selected on BG blood agar containing 100 μg/ml streptomycin and 10 μg/ml gentamycin. The resulting strain was named BPZM2e-ΔFHA.

The absence of FHA in BPZM2e-ΔFHA was verified by SDS-PAGE and straining by Coomassie blue, and the presence of Fha44-3M2e in the culture supernatant was determined by immunoblot analysis. SDS-PAGE and Coomassie blue staining showed the absence of the 220-kDa protein, corresponding to FHA in the culture supernatant of the mutant strain, as well as in that of BPGR4, a known FHA-deficient strain, used as a control. The immunoblot analysis of unconcentrated culture supernatants indicated that the FHA-deficient mutant produced at least as much Fha44-3M2e as the BPZM2e parent strain. As expected, no immunreactive band was detected in the culture supernatant of BPZE1.

Lung Colonization of Mice by BPZM2e-ΔFHA

To investigate the colonization profile of the new recombinant strain after deletion of FHA, BALB/c mice were infected i.n. with $10^7$ CFU of BPZM2e-ΔFHA, and the bacterial load in the lungs was followed for up to 28 days. Both BPZE1 and BPZM2e-ΔFHA colonized the lungs and persisted in the lungs of the mice at similar levels, although at day 3 after inoculation significantly less BPZM2e-ΔFHA than BPZE1 was detected in the lungs of the mice.

Immunogenicity of BPZM2e-ΔFHA

Figure 1:
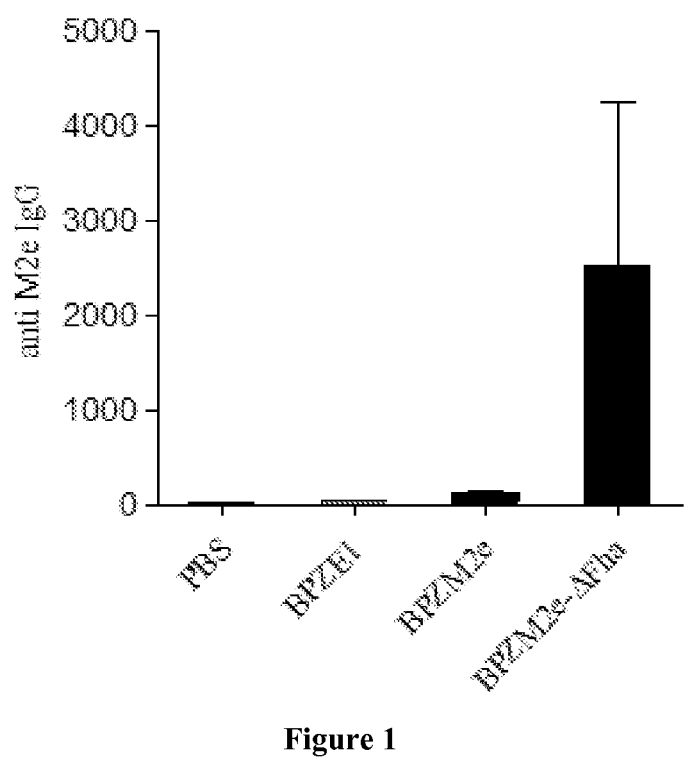

The immunogenicity of BPZM2e-ΔFHA was evaluated after two i.n. administrations at a 4-week interval. The sera were collected 2 weeks after the last immunization, and the systemic anti-M2e antibody response was analyzed. BPZM2e-ΔFHA was found to induce high levels of systemic IgG against M2e, whereas two administrations of BPZM2e producing FHA or BPZE1 did not result in a significant anti-M2e IgG response (FIG. 1), as expected. These observations indicate that the absence of FHA strongly increases the immune responses to M2e after i.n. immunization with recombinant BPZE1.

2. Recombinant BPZE1 Strain Producing Fha44-$G_{RSV}$(BPZ$G_{RSV}$)

Construction of Recombinant BPZE1 Strain Producing Fha44-$G_{RSV}$ (BPZ$G_{RSV}$)

A peptide fragment of the G protein of RSV spanning amino-acid residues 170 to 197 has been shown to contain a neutralizing B cell epitope (Power et al., 2001; Yusibov et al., 2005) and a T cell epitope (Varga et al., 2000). This region of the protein is also well conserved among different RSV isolates. As for the M2e epitope of the influenza virus above, we have used Fha44 as carrier to express the G epitope in BPZE1.

A single copy of the G epitope-encoding sequence was fused to the Fha44-encoding sequence. The construct was inserted into the BPZE1 chromosome at the dnt locus by allelic exchange, placing the transgene under the control of the dnt promoter in the recombinant strain named BPZ$G_{RSV}$.

Unconcentrated culture supernatants of BPZ$G_{RSV}$ were examined by immunoblot analysis using an anti-G monoclonal antibody. An approximately 90-kDa band, corresponding to the expected size of the Fha44-$G_{RSV}$ chimeric protein, was detected in the culture supernatant of the recombinant strain, indicating that the chimeric protein was secreted from the recombinant strain.

Lung Colonization and Immunogenicity of BPZ$G_{RSV}$

To study the ability of the recombinant strain BPZ$G_{RSV}$ to colonize the murine respiratory tract, BALB/c mice were infected i.n. with $10^6$ CFU of BPZ$G_{RSV}$ or with non-recombinant BPZE1, and their colonization profiles were compared. The colonization profile of recombinant strain BPZ$G_{RSV}$ was indistinguishable to that of the corresponding parental strain BPZE1 indicating that the insertion of Fha44-$G_{RSV}$ does not alter the ability to colonize the lungs of mice.

The antibody responses to the G peptide were examined by ELISA after administration of BPZ$G_{RSV}$. However, no G-specific antibodies were detected. The BPZ$G_{RSV}$ dose was then increased ten-fold, and BALB/c mice were i.n. immunized twice at a 4-week interval with $10^7$ CFU of BPZE1 or recombinant BPZ$G_{RSV}$. Sera were collected 2 weeks after the last immunization to evaluate the systemic anti-G IgG responses. Again, no significant antibody response to the G peptide was detected in sera.

Mutation of FHA and Characterization of the New Recombinant Strain (BPZG$_{RSV}$-ΔFHA)

The chromosomal gene coding for FHA (fhaB) was then inactivated from BPZG$_{RSV}$ by introducing the pFus2 derivative as described above, and the absence of FHA in BPZG$_{RSV}$-ΔFHA was verified by SDS-PAGE and straining by Coomassie blue, and the presence of Fha44-G$_{RSV}$ in the culture supernatant was determined by immunoblot analysis. SDS-PAGE and Coomassie blue staining showed the absence of the 220-kDa protein, corresponding to FHA in the culture supernatant of the mutant strain. The immunoblot analysis of unconcentrated culture supernatants indicated that the FHA-deficient mutant strain produced as much Fha44-G$_{RSV}$ as the BPZG$_{RSV}$ parent strain.

Immunogenicity of BPZG$_{RSV}$-ΔFHA

The immunogenicity of BPZG$_{RSV}$-ΔFHA was evaluated after two i.n. administrations at a 4-week interval. The sera were collected 2 weeks after the last immunization, and the systemic anti-G antibody response was analyzed by ELISA. BPZG$_{RSV}$-ΔFHA was found to induce high levels of systemic IgG against the G epitope, whereas two administrations of BPZE1 or BPZG$_{RSV}$ producing FHA did not result in a significant anti-G IgG response (FIG. 2). These observations indicate that, as for M2e, the absence of FHA strongly increases the immune responses to the G epitope after i.n. immunization with recombinant BPZE1

3. Recombinant BPZE1 Strain Producing Fha44-PcsB (BPZPcsB)

Construction of Recombinant BPZE1 Strain Producing Fha44-PcsB (BPZPcsB)

PcsB is a protein antigen of *S. pneumoniae* that is highly conserved among various clinical isolates and induces protection against lethal sepsis. It has been shown to be cross-protective against four different serotypes in both sepsis and pneumonia models (Giefing et al., 2008).

The gene coding the mature portion of PcsB (from amino acid 28 to 278) was fused as a single copy to the Fha44-encoding sequence. The construct was inserted into the BPZE1 chromosome at the dnt locus by allelic exchange, placing the transgene under the control of the dnt promoter in the recombinant strain named BPZPcsB.

Unconcentrated culture supernatants of BPZPcsB were examined by SD-PAGE and Coomassie-blue staining. A 112-kDa band, corresponding to the Fha44-PcsB chimeric protein, was readily detectable in the unconcentrated culture supernant of the recombinant strain, indicating that the chimeric protein was secreted from the recombinant strain.

Immunogenicity of BPZPcsB

BALB/C mice were nasally immunized three times at 4-weeks intervals with $10^7$ cfu BPZPcsB or received BPZE1 as a control. Sera were collected two weeks after each immunization, and the antibody responses to PcsB were examined by ELISA. Increasing doses of BPZPcsB resulted in increasing antibody titers to PcsB, although the antibody titers remained rather low, especially after the first and second immunization.

Mutation of FHA and Characterization of the New Recombinant Strain (BPZPcsB-ΔFHA)

The chromosomal gene coding for FHA (fhaB) was then inactivated from BPZPcsB by introducing the pFus2 derivative as described above, and the absence of FHA in BPZ-PcsB-ΔFHA, but the presence of Fha44-PcsB was verified by SDS-PAGE and straining by Coomassie blue. SDS-PAGE and Coomassie blue staining showed the absence of the 220-kDa protein, corresponding to FHA, and the presence of a lower Mr protein, corresponding to Fha44-PcsB, in the culture supernatant of the mutant strain.

Immunogenicity of BPZPcsB-ΔFHA

Figure 3:
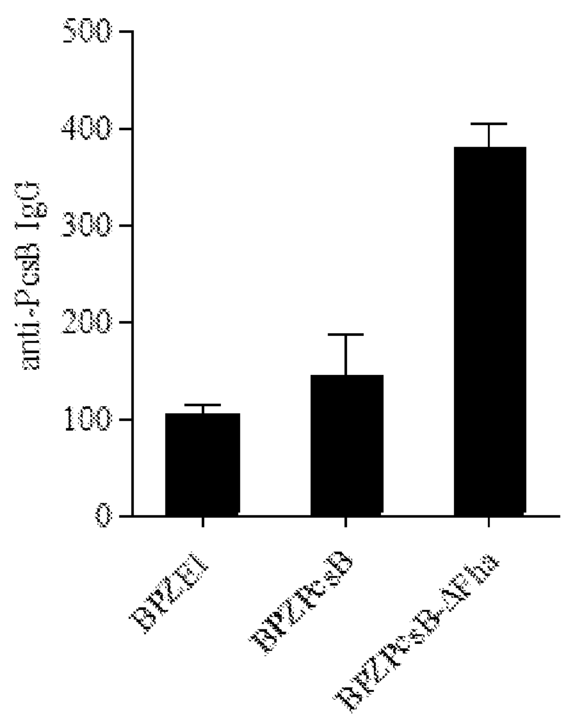
FIG. 3. Serum anti-PcsB IgG responses after administration of the indicated BPZE1 derivatives. BALB/c mice were i.n. immunized twice at a 4-week interval with $10^7$ CFU of the indicated strains. Sera were collected two weeks after the last immunization, and serum IgG responses to PcsB were measured by ELISA.

The immunogenicity of BPZPcsB-ΔFHA was evaluated after two i.n. administrations at a 4-week interval. The sera were collected 2 weeks after the last immunization, and the systemic anti-PcsB antibody responses were analyzed. BPZ-PcsB-ΔFHA was found to induce high levels of systemic IgG against PcsB that were significantly higher than those induced by BPZPcsB producing FHA (FIG. 3). These observations indicate that, as for M2e and GRSV the absence of FHA significantly increases the immune responses to PcsB after i.n. immunization with recombinant BPZE1.

Throughout this application, various references describe the state of the art to which this invention pertains. The disclosures of these references are hereby incorporated by reference into the present disclosure.

REFERENCES

Alonso S, Willery R, Renauld-Mongenie G, Locht C. 2005. Production of Non typeable *Haemophilus* influenzae HtrA by Recombinant *Bordetella pertussis* with the Use of Filamentous Hemagglutinin as a Carrier. Infect. Immun., 73, 4295-4301

Antoine R, and Locht C. 1990. Roles of the disulfide bond and the carboxy-terminal region of the S1 subunit in the assembly and biosynthesis of pertussis toxin. Infect, Immun., 58, 1518-1526.

Antoine R, Alonso S, Raze D, Coutte L, Lesjean S, Willery E, et al. 2000. New virulence-activated and virulence-repressed genes identified by systematic gene inactivation and generation of transcriptional fusions in *Bordetella pertussis*. J Bacteriol 182, 5902-5905.

Coppens I, Alonso S, Antoine R, Jacob-Dubuisson F, Renauld-Mongenie G, Jacobs E, Locht C. 2001. Production of *Neisseria meningitides* transferrin-binding protein B by recombinant *Bordetella pertussis*, Infect. Immun. 69, 5440-5446, De Filette M, Fiers W, Martens W, Birkett A, Ramne A, Lowenadler B, et al. 2006. Improved design and intranasal delivery of an M2e-based human influenza A vaccine. Vaccine 24, 6597-6601.

Feunou P F, Kammoun H, Debrie A S, Mielcarek N, Locht C. 2010. Long-term immunity against pertussis induced by a single nasal administration of live attenuated *B. pertussis* BPZE1. Vaccine 28, 7047-7053.

Giefing C., Meinke, A L, Hanner M, Henics T, Minh D B, Gelbmann D, Lundberg U, Senn B M, Schunn M, Habel, A, Henriques-Normark B, Örtqvist A, Kahn M, von Gabain A, and Nagy E. 2008. Discovery of a novel class of highly conserved vaccine antigens using genomic scale antigenic fingerprinting of pneumococcus with human antibodies. J Exp Med 205, 117-131.

Ho, S. Y., Chua, S. Q., Foo, D. G. W., Locht, C., Chow, V. T., Poh, C. L., and Alonso, S. 2008. Highly attenuated *Bordetella pertussis* strain BPZE1 as a potential live vehicle for delivery of heterologous vaccine candidates. Infect Immun 76, 111-119.

Huang C C, Chen P M, Kuo J K, Chui W H, Lin S T et al. 1962. Experimental whooping cough. N Engl J Med 266, 105-111.

Kashimoto T., Katahira J, Cornejo W R, Masuda M, Fukuoh A, Matsuzawa T, Ohnishi T, Horiguchi Y. (1999) Identification of functional domains of *Bordetella* dermonecrotizing toxin. Infect. Immun. 67: 3727-32.

Kavanagh H, Noone C, Cahill E, English K, Locht C, Mahon B P. 2010. Attenuated *Bordetella pertussis* vaccine strain BPZE1 modulates allergen-induced immunity and prevents allergic pulmonary pathology in a murine model. Clin Exp Allergy 40, 933-941.

Laemmli U K. 1970. Cleavage of structural proteins during the assembly of the head of bacteriophage T4. Nature 227, 680-685.

Lambert-Buisine, C., E. Willery, C. Locht, and F. Jacob-Dubuisson. 1998. N-terminal characterization of the *Bordetella pertussis* filamentous haemagglutinin. Mol. Microbiol. 28, 1283-1293.

Li, R., Lim, A., Ow, S. T., Phoon, M. C., Locht, C., Chow, V. T., and Alonso, S. 2011. Development of live attenuated *Bordetella pertussis* strains expressing the universal influenza vaccine candidate M2e. Vaccine 29, 5502-5511.

Li R, Lim A, Phoon M C, Narasaraju T, Ng J K, Poh W P, Sim M K, Chow V T, Locht C, Alonso S. 2010. Attenuated *Bordetella pertussis* protects against highly pathogenic influenza A viruses by dampening the cytokine storm. J Virol 84, 7105-7113.

Locht C, Antoine R, Jacob-Dubuisson F. 2001. *Bordetella pertussis*, molecular pathogenesis under multiple aspects. Cur Opin Microbiol 4, 82-89.

Locht C, Geoffroy M C, Renauld G. 1992. Common accessory genes for the *Bordetella pertussis* filamentous hemagglutinin and fimbriae share sequence similarities with the papC and papD gene families. EMBO J 11, 3175-3183.

Mascart F, Verscheure V, Malfroot A, Hainaut M, Piérard D, Temerman S, Peltier A, Debrie A S, Levy J, Del Giudice G, Locht C. 2003. *Bordetella pertussis* infection in 2-months-old infants promotes Type 1 T cell responses. J Immunol 170, 1504-1509.

Mekseepralard C, Toms G L, Routledge E G. 2006. Protection of mice against human respiratory syncytial virus by wild-type and aglycosyl mouse-human chimaeric IgG antibodies to subgroup-conserved epitopes on the G glycoprotein. J Gen Virol 87, 1267-1273.

Menozzi F D, Gantiez C, Locht C. 1991. Identification and purification of transferrin- and lactoferrin-binding proteins of *Bordetella pertussis* and *Bordetella bronchiseptica*. Infect Immun 59, 3982-3988.

Mielcarek N, Debrie A S, Mahieux S, Locht C. 2010. Dose-response of attenuated *Bordetella pertussis* BPZE1-induced protection in mice. Clin Vaccine Immunol 17, 317-324.

Mielcarek N, Debrie A S, Raze D, Bertout J, Rouanet C, Ben Younes A, Creuzi C, Engle J, Goldman W E, Locht C. 2006. Live attenuated *B. pertussis* as a single single-dose nasal vaccine against whooping-cough. PLoS Pathog 2, 662-670.

Mutsch, M., Zhou, W., Rhodes, P., Bopp, M., Chen, R. T., Linder, T., Spyr, C., Steffen, R. 2004. Use of the inactivated intranasal influenza vaccine and the risk of Bell's palsy in Switzerland. N Engl J Med 350, 896-903.

Neirynck S, Deroo T, Saelens X, Vanlandschoot P, Jou W M, Fiers W. 1999. A universal influenza A vaccine based on the extracellular domain of the M2 protein. Nat Med 5, 1157-1163.

Quandt J, Hynes M F. 1993. Versatile suicide vectors which allow direct selection for gene replacement in gram-negative bacteria. Gene 127, 15-21.

Power U F, Plotnicky-Gilquin H, Goetsch L, Champion T, Beck A, Haeuw J F, Nguyen T N, Bonnefoy J Y, Corvaia N. 2001. Identification and characterization of multiple linear B cell protectopes in the respiratory syncytial virus G protein. Vaccine 19, 2345-2351.

Renauld-Mongenie G, Cornette J, Mielcarek N, Menozzi F D, Locht C. 1996. Distinct roles of the N-terminal and C-terminal precursor domains in the biogenesis of the *Bordetella pertussis* filamentous hemagglutinin. J Bacteriol 178, 1053-1060.

Reveneau N, Alonso S, Jacob-Dubuisson F, Mercenier A, Locht C. 2001. Tetanus toxin fragment C-specific priming by intranasal infection with recombinant *Bordetella pertussis*. Vaccine 20, 926-933.

Simon R, Priefer U, Pühler A. 1983. A broad host range mobilization system for in vivo genetic engineering: transposon mutagenesis in Gram-negative bacteria. Bio/technology I, 784-791.

Skerry C M, Cassidy J P, English K, Feunou-Feunou P, Locht C, Mahon B P. 2009. A live attenuated *Bordetella pertussis* candidate vaccine does not cause disseminating infection in gamma interferon receptor knockout mice. Clin Vaccine Immunol 16, 1344-1351.

Stainer D W, Scholte M J. 1970. A simple chemically defined medium for the production of phase I *Bordetella pertussis*. J Gen Microbiol 63, 211-220.

Stibitz R. 1994. Use of conditionally counterselectable suicide vectors for allelic exchange. Methods Enzymol 235, 458-465.

Varga S M, Wissinger E L, Braciale T J. 2000. The attachment (G) glycoprotein of respiratory syncytial virus contains a single immunodominant epitope that elicits both Th1 and Th2 CD4+ T cell responses. J Immunol 165, 6487-6495.

Yusibov, V., V. Mett, V. Mett, C. Davidson, K. Musiychuk, S. Gilliam, A. Farese, T. MacVittie, and D. Mann. 2005. Peptide-based candidate vaccine against respiratory syncytial virus. Vaccine 23:2261-2265;

TABLE 1

| Bacterial strains | |
|---|---|
| Strains | Description (reference) |
| BPSM | $Sm^R$ virulent *B. pertussis* (Menozzi et al., 1991) |
| BPGR4 | $Sm^R$ strain derived from BPSM and FHA deficient (Locht et al., 1992) |
| BPZE1 | $Sm^R$ attenuated strain derived from BPSM (Mielcarek et al., 2006) |
| BPZM2e | BPZE1 recombinant strain expressing Fha44-$(M2e)_3$ (this work) |
| BPZM2e-ΔFha | BPZE1 recombinant strain expressing Fha44-$(M2e)_3$ and FHA deficient (this |
| $BPZG_{RSV}$ | work) |
| $BPZG_{RSV}$-ΔFha | BPZE1 recombinant strain expressing Fha44-$G_{RSV}$ (this work) |
| BPZPcsB | BPZE1 recombinant strain expressing Fha44-$G_{RSV}$ and FHA deficient (this |
| BPZPcsB-ΔFha | work) |
| | BPZE1 recombinant strain expressing Fha44-PcsB (this work) |
| | BPZE1 recombinant strain expressing Fha44-PcsB and FHA deficient (this work) |

What is claimed is:

1. A live attenuated *Bordetella pertussis* strain comprising a mutated pertussis toxin (ptx) gene, a deleted dermonecrotic toxin (dnt) gene, a heterologous ampG gene, an inactivated filamentous haemagglutinin (FHA) gene, and a gene encoding a hybrid protein comprising an N-terminal fragment of filamentous haemagglutinin (FHA) and a heterologous antigen, wherein the gene encoding the hybrid protein is inserted into the locus of the deleted dnt gene and the *Bordetella pertussis* strain lacks a native FHA protein.

2. The *Bordetella pertussis* strain of claim 1, wherein the mutated ptx gene comprises at least one mutation leading to an enzymatically inactive protein that retains immunogenic properties.

3. The *Bordetella pertussis* strain of claim 1, wherein the ampG gene is replaced with a heterologous ampG gene leading to a residual tracheal cytotoxin (TCT) activity of less than 5%.

4. The *Bordetella pertussis* strain of claim 3, wherein the heterologous ampG gene is from *E. coli.*

5. The *Bordetella pertussis* strain of claim 1, wherein the heterologous antigen comprises at least one epitope of a protein expressed by a pathogen responsible for an infection of the respiratory tract.

6. The *Bordetella pertussis* strain of claim 1, wherein the hybrid protein comprises the N-terminal fragment of FHA fused to the extracellular domain of the matrix protein (Me2) of the influenza A virus.

7. The *Bordetella pertussis* strain of claim 1, wherein the hybrid protein comprises the N-terminal fragment of the FHA protein fused to three copies of the extracellular domain of the matrix protein (Me2) of the influenza A virus.

8. The *Bordetella pertussis* strain of claim 1, wherein the hybrid protein comprises the N-terminal fragment of the FHA protein fused to at least an antigenic fragment of the G protein of the Respiratory Syncytial Virus (SRV).

9. The *Bordetella pertussis* strain of claim 1, wherein the hybrid protein comprises the N-terminal fragment of the FHA protein fused to an antigenic fragment of the PcsB protein of *S. pneumoniae.*

10. A method for enhancing the immune response toward a microbial pathogen in a subject, the method comprising administering to a subject the live attenuated *Bordetella pertussis* strain comprising a mutated pertussis toxin (ptx) gene, a deleted dermonecrotic toxin (dm) gene, a heterologous ampG gene, an inactivated filamentous haemagglutinin (FHA) gene, and a gene encoding a hybrid protein comprising an N-terminal fragment of filamentous haemagglutinin (FHA) and a heterologous antigen, wherein the gene encoding the hybrid protein is inserted into the locus of the deleted dnt gene and the *Bordetella pertussis* strain lacks a native FHA protein, and wherein the heterologous antigen comprises an antigen from the microbial pathogen.

11. The *Bordetella pertussis* strain of claim 10, wherein the microbial pathogen is an influenza virus.

12. The *Bordetella pertussis* strain of claim 10, wherein the microbial pathogen is a Respiratory Syncytial Virus (SRV).

13. The *Bordetella pertussis* strain of claim 10, wherein the microbial pathogen is *Streptococcus pneumoniae.*

* * * * *

UNITED STATES PATENT AND TRADEMARK OFFICE

CERTIFICATE OF CORRECTION

PATENT NO. : 9,528,086 B2
APPLICATION NO. : 14/682155
DATED : December 27, 2016
INVENTOR(S) : Camille Locht et al.

It is certified that error appears in the above-identified patent and that said Letters Patent is hereby corrected as shown below:

In the Claims

Column 30, Lines 59-65, Claims 11-13: Delete the preamble "The Bordetella pertussis strain" from each of Claims 11-13 and replace with the following preamble "The method,".

Signed and Sealed this
Eleventh Day of April, 2017

Michelle K. Lee
*Director of the United States Patent and Trademark Office*